United States Patent [19]

Damani

[11] Patent Number: 5,084,267

[45] Date of Patent: Jan. 28, 1992

[54] SUSTAINED RELEASE COMPOSITIONS FOR TREATING PERIODONTAL DISEASE

[75] Inventor: Nalinkant C. Damani, Cincinnati, Ohio

[73] Assignee: The Procter & Gamble Company, Cincinnati, Ohio

[21] Appl. No.: 438,545

[22] Filed: Nov. 17, 1989

[51] Int. Cl.$^5$ .................. A61K 9/20; A61K 31/65; A61K 31/78

[52] U.S. Cl. .................. 424/426; 424/435; 514/152; 514/900; 514/902

[58] Field of Search .................. 424/81, 435

[56] References Cited

U.S. PATENT DOCUMENTS

| | | | |
|---|---|---|---|
| 3,867,190 | 2/1975 | Schmitt et al. | 117/138.8 |
| 4,226,848 | 10/1980 | Nagai et al. | 424/19 |
| 4,250,163 | 2/1981 | Nagai et al. | 424/14 |
| 4,454,110 | 6/1984 | Caslavsk et al. | 424/54 |
| 4,568,535 | 2/1986 | Loesche | 514/365 |
| 4,568,536 | 2/1986 | Kronenthal et al. | 424/22 |
| 4,569,837 | 2/1986 | Suzuki et al. | 424/28 |
| 4,603,076 | 7/1986 | Bowditch et al. | 428/246 |
| 4,615,697 | 10/1986 | Robinson | 604/890 |
| 4,644,018 | 2/1987 | Bowditch et al. | 521/130 |
| 4,650,665 | 3/1987 | Kronenthal et al. | 424/435 |
| 4,670,252 | 6/1987 | Sampathkumar | 424/53 |
| 4,685,883 | 8/1987 | Jernberg | 433/215 |
| 4,699,823 | 10/1987 | Kellenberger et al. | 428/219 |
| 4,725,628 | 2/1988 | Garvey et al. | 521/137 |
| 4,725,629 | 2/1988 | Garvey et al. | 521/137 |
| 4,764,377 | 8/1988 | Goodson | 424/435 |
| 4,769,414 | 9/1988 | Kightlinger et al. | 525/54.24 |
| 4,795,436 | 1/1989 | Robinson | 424/422 |
| 4,818,534 | 4/1989 | Levy | 424/404 |
| 4,839,215 | 6/1989 | Starling et al. | 428/131 |
| 4,863,970 | 9/1989 | Patel et al. | 514/784 |
| 4,892,736 | 1/1990 | Goodson | 424/435 |
| 4,900,552 | 2/1990 | Sanvordeker et al. | 424/422 |
| 4,900,554 | 2/1990 | Yanagibashi et al. | 424/448 |
| 4,933,182 | 6/1990 | Higashi et al. | 424/435 |

FOREIGN PATENT DOCUMENTS

| | | |
|---|---|---|
| 140766 | 5/1985 | European Pat. Off. . |
| 241178 | 10/1987 | European Pat. Off. . |
| 297535 | 1/1989 | European Pat. Off. . |
| 63-79817 | 4/1988 | Japan . |
| 63-287719 | 11/1988 | Japan . |

Primary Examiner—Shep K. Rose
Attorney, Agent, or Firm—Douglas C. Mohl; Kim William Zerby; Richard C. Witte

[57] ABSTRACT

This invention relates to compositions/devices and methods for treating diseases of the oral cavity in humans and lower animals using polypropenoic acid compositions/devices for releasing drugs in the oral cavity.

5 Claims, No Drawings

SUSTAINED RELEASE COMPOSITIONS FOR TREATING PERIODONTAL DISEASE

TECHNICAL FIELD

This invention relates to compositions/devices for treating diseases of the oral cavity, which compositions/devices are placed in or around the periodontal pocket. The invention also relates to methods of using the compositions/devices in humans and lower animals suffering from such diseases.

Periodontal disease, for example, is a major cause of tooth loss in adults. Tooth loss from periodontal disease is a significant problem beginning at age 35, but even by age 15 it is estimated that about 4 out of 5 persons already have gingivitis and 4 out of 10 have periodontitis.

While good oral hygiene, as achieved by brushing the teeth with a cleansing dentifrice, may help reduce the incidence of periodontal disease, it does not necessarily prevent or eliminate its occurrence. This is because microorganisms contribute to both the initiation and progress of periodontal disease. Thus, in order to prevent or treat periodontal disease, these microorganisms must be suppressed by some means other than simple mechanical scrubbing. Towards this end, there has been a great deal of research aimed at developing therapeutic dentifrices, mouthwashes, and methods of treating periodontal disease which are effective in suppressing these microorganisms.

Recent developments in the art are directed toward delivering the therapeutic agent directly to the periodontal pocket, in some cases in a controlled release formulation. Gordon et al. have described the use of a drug-filled polymer hollow fiber. (J. M. Goodson et al., "Periodontal Therapy by Local Delivery of Tetracycline", *J. Clin. Periodontal.* 6, 83 (1979), J. Lindhe et al., "Local Tetracycline Delivery Using Hollow Fiber Devices in Periodontal Therapy", *J. Clin. Periodontal.* 6, 141 (1979) and R. L. Dunn et al., "Monolithic Fibers for Controlled Delivery of Tetracycline", in *Proc. Ninth Int. Symposium on Controlled Release of Bioactive Materials*, Ft. Lauderdale, FL, July (1982). This device is tied around a tooth and gently pressed below the margin of the gingiva so that it resides in the periodontal pocket, and is capable of delivering an effective dose of 2.5 micrograms of tetracycline per day per periodontal pocket for a prolonged period of a week or more. Similar results have been obtained by Coventry and Newman (J. Coventry and H. N. Newman, "Experimental Use of a Slow Release Device Employing Chlorhexidine Gluconate in Areas of Acute Periodontal Inflammation", *J. Clin. Periodontal.* 9, 129 (1982) and Addy et al. (M. Addy et al., "The Development and in vitro Evaluation of Acrylic Strips and Dialysis Tubing for Local Drug Delivery", *J. Periodontal* 53, 693 (1982) using acrylic strips 1 mm or more long, impregnated with chlorhexidine, tetracycline or metronidazole, which were inserted into the periodontal pocket with tweezers. Such a strip, formed from ethylcellulose impregnated with metronidazole, is disclosed by Loesche in U.S. Pat. No. 4,568,538 (February 1986). Another strip, employing a water soluble polymer of a particular elasticity and viscosity, is disclosed by Suzuki et al. in U.S. Pat. No. 4,569.837.

In addition to the above approaches, the prior art also discloses using putty-like compositions containing an antimicrobial for insertion into the periodontal pocket. See U.S. Pat. No. 4,650,665, Mar. 17, 1987 to Kronenthal et al., incorporated herein by reference.

The present inventor has discovered that using polypropenoic acid as the material forming the composition/device allows for efficient/good devices to be formed.

Previous attempts to effectively treat periodontal pockets have not been desirably successful. This is largely due to the fact that a periodontal pocket cavity is very narrow and convoluted or tortuous, making it nearly impossible to fill the entire cavity with a treatment product.

This invention, utilizing highly swellable polymer eliminates such problems. Once a product of this invention is placed in periodontal cavity, the polymer swells, expands, and reaches narrow crevices and furcations of the treated cavity, carrying active agent throughout the cavity. This provides most desirable efficacy at treatment site.

It is therefore an object of the present invention to provide polypropenoic compositions/devices suitable for treating periodontal disease and other diseases of the oral cavity.

It is a further object of the present invention to provide such compositions/devices using mixtures of polypropenoic acid and other polymers.

It is still a further object of the present invention to provide a method of treating periodontal disease.

All percentages and ratios used in here are by weight unless otherwise indicated.

All measurements are made at 25° C. unless otherwise indicated.

SUMMARY OF INVENTION

The present invention relates to compositions/devices and methods for treating diseases of the oral cavity by inserting the compositions/devices around or into the periodontal pocket of humans and lower animals. The compositions/devices comprise polypropenoic acid and an agent providing relief of diseases of the oral cavity such as periodontal disease.

DETAILED DESCRIPTION OF THE INVENTION

The essential as well as optional components of the compositions/devices of this invention are described below.

Polymer

The polymer used in the present compositions is referred as super absorbent polymer and is defined as polypropenoic acid. The material is a polyacrylic acid which is lightly crosslinked with an agent such as divinyl glycol, trimethylpropane triacrylate and polyallyl sucrose. These materials are provided as Dry Tech 512 by Dow Chemical Company, Aqualac-CA by Nippon Shokubai and NALCO-1181 by Nalco Chemicals. Other materials related to the above include Polycarbophil by B. F. Goodrich Company.

A preferred material is Dry Tech-512 which is polyacrylic acid crosslinked with 0.004 mole percent of trimethylpropane triacrylate. The carboxylic groups can be neutralized with, for example, a sodium base to an extent of 75% or more.

A most preferred polymer useful in the present invention has very high, nearly infinite molecular weight in its crosslinked form which is estimated to be 2 million to 10 million or even higher. Unit segments of crosslinked polymer have a range of number average molecular weight from about 50,000 to about 1 million. The polymer is used in the present compositions at a level of from about 1% to about 99%, preferably from about 10% to about 75%, most preferably from about 20% to about 50%.

Drug Active

The drugs useful for use in the present compositions/devices are varied and many and include any agent which provides treatment of the disease. Some therapeutic agents which are amenable to delivery by this means and are potentially of value for periodontal therapy, include (but are not limited to) antimicrobial-/antibacterial agents such as iodine, sulfonamides, mercurials, bisbiguanides, or phenolics; antibiotics such as tetracycline, neomycin, kanamycin, metronidazole, or clindamycin; antiinflammatory agents such as aspirin, naproxen, ibuprofen, flurbiprofen, indomethacin, eugenol, or hydrocortisone; immune-suppressive or stimulatory agents such as methotrexate or levamasole; dentinal desensitizing agents such as strontium chloride or sodium fluoride; odor masking agents such as peppermint oil or chlorphyll; immune reagents such as immunoglobulin or antigens; local anesthetic agents such as lidocaine or benzocaine; nutritional agents such as amino acids, essential fats, and vitamin C; antioxidants such as alphatocopherol and butylated hydroxy toluene; lipopolysaccharide complexing agents such as polymyxin; or peroxides such as urea peroxide. It is recognized that in certain forms of therapy, combinations of these agents in the same delivery system may be useful in order to obtain an optimal effect. Thus, for example, an antibacterial and an antiinflammatory agent may be combined in a single delivery system to provide combined effectiveness.

The drug active is used at a level of from about 1% to about 99%, preferably from about 5% to about 75%, most preferably from about 10% to about 50% of the compositions/devices. The compositions/devices, for example, are designed to release drug at a rate to provide concentration of from about 10 $\mu$g to about 2000 $\mu$g, preferably from about 50 $\mu$g to about 1000 $\mu$g, most preferably from about 100 $\mu$g to about 500 $\mu$g per milliliter of the gingival crevicular fluid of a treated periodontal pocket. Desired release rates can be achieved by altering ratios of components in a composition.

Optional Components

In addition to the drug active, the compositions/devices of the present invention may include a variety of optional components. Such components include, but are not limited to, surfactants, other polymers, viscosity controlling agents, complexing agents, antioxidants, gums such as guar gum, waxes/oils such as castor wax, castor oil, glycerol, dibutyl phthalate and ethyl sebacate as well as many others.

The additional polymer may include a number of polymers such as methyl cellulose, polycaprolactone and polylactide. A particularly preferred polymer is a copolymer of lactide and glycolide. Lactide monomeric species preferably comprise 15% to about 85%, most preferably from about 35% to about 65%, of the polymers while glycolide monomers comprise from about 15% to about 85% of the polymer, preferably from about 35% to about 65% on a molar basis. The molecular weight lies in the range of from about 1000 to about 120,000 (number average). These polymers are described in detail in U.S. Pat. No. 4.443.430, Apr. 17, 1984, to Mattei incorporated herein by reference.

If used, these optional components comprise from about 0.1% to about 50%, preferably from about 0.5% to about 25% of the total composition/device.

METHOD OF MANUFACTURE

Method of manufacturing the compositions/devices of this invention are disclosed in the Examples.

The following Examples further describe and demonstrate the preferred embodiments within the scope of the present invention. The Examples are given solely for the purpose of illustration and are not to be constructed as limitations of the present invention as many variations thereof are possible without departing from its spirit and scope.

EXAMPLE I

The following is an exemplary composition/device of the present invention.

|  | Weight % |
| --- | --- |
| Tetracycline hydrochloride | 50 |
| Polypropenoic acid | 22.7 |
| Poly(lactyl-co-glycolide)/50:50 copolymer | 22.7 |
| Propylene Carbonate | 4.6 |

The above composition can be prepared in a number of different ways. One way is as follows: Polymer is charged into 110° C., electrically heated mixer, equipped with high shear Sigma type rotor blades. Propylene carbonate is added and mixed into the polymer. The drug is added and mixed until uniform. The drug polymer blend is removed for further processing into desired size and shaped devices.

The compositions/devices of the invention of this application are inserted into or around the periodontal pocket or gingival region, and are administered in the form of a particle, film or sheet. The size, shape, and thickness can be changed according to the condition of the periodontal disease to be treated and they are not particularly critical. Ordinarily, the size, shape, and thickness are changed according to the size of the periodontal pocket of the patient or the condition of the gingiva. The devices may be for example of a size such that the thickness is in the range of 0.01 to 2 mm, preferably from about 0.1 to about 1 mm; the width in the range of 0.1 to about 5 mm, preferably from about 0.2 to about 4 mm; and the length in the range of from about 1 to about 15 mm, preferably from about 3 to about 10 mm.

EXAMPLE II

Given below is another composition/device of the present invention:

|  | Wt. % |
| --- | --- |
| Chlorhexidine acetate | 40 |
| Polypropenoic acid | 35 |
| Methyl Cellulose | 20 |
| Glycerol monostearate | 5 |

EXAMPLE III

Given below is still another composition/device representative of the present invention:

|  | Wt. % |
| --- | --- |
| Metronidazole | 40 |
| Polypropenoic acid | 30 |
| Polycaprolactone | 25 |
| Pluronic F-68 | 5 |

EXAMPLE IV

Given below is still another composition representative of the present invention:

|  | Wt. % |
| --- | --- |
| Flurbiprofen | 20 |
| Polypropenoic acid | 25 |
| Xanthan Gum | 20 |
| Polylactide polymer | 25 |
| Polyethylene glycol | 10 |

I claim:

1. A composition suitable for insertion into or around the periodontal pocket of a person or lower animal suffering from diseases of the oral cavity comprising polypropenoic acid crosslinked with less than about 0.004 mole percent of crosslinking agent and a tetracycline drug active.

2. A composition according to claim 1 wherein the concentration of the drug active is from about 10% to about 50%.

3. A composition according to claim 1 which in addition contains another polymer.

4. A method of treating periodontal disease in a person or lower animal suffering from such disease by placing a composition according to claim 1 into the periodontal pocket of said person or lower animal.

5. A method according to claim 4 wherein the composition is formed into a shape having a width of from about 0.1 mm to about 5 mm, a thickness of from about 0.01 mm to about 2 mm and a length of from about 1 mm to about 15 mm.

* * * * *